United States Patent
Cheng

(10) Patent No.: US 6,470,068 B2
(45) Date of Patent: Oct. 22, 2002

(54) X-RAY COMPUTER TOMOGRAPHY SCANNING SYSTEM

(76) Inventor: Chin-an Cheng, 1389 Guazdar Ct., Santa Clara, CA (US) 95051

( * ) Notice: Subject to any disclaimer, the term of this patent is extended or adjusted under 35 U.S.C. 154(b) by 0 days.

(21) Appl. No.: 09/905,614

(22) Filed: Jul. 13, 2001

(65) Prior Publication Data

US 2002/0097831 A1 Jul. 25, 2002

Related U.S. Application Data

(60) Provisional application No. 60/262,841, filed on Jan. 19, 2001.

(51) Int. Cl.[7] ............................................. H05G 1/00
(52) U.S. Cl. ........................................... 378/20; 378/10
(58) Field of Search ................... 378/4, 10, 20, 378/68, 69, 208

(56) References Cited

U.S. PATENT DOCUMENTS

| | | | |
|---|---|---|---|
| 4,298,800 A | 11/1981 | Goldman | 250/445 |
| 4,422,177 A | 12/1983 | Mastronardi et al. | 378/17 |
| 4,472,822 A | 9/1984 | Swift | 378/10 |
| 4,651,335 A * | 3/1987 | Kalender et al. | 378/163 |
| 5,023,895 A | 6/1991 | McCroskey et al. | 378/4 |
| 5,036,530 A | 7/1991 | DiGiovanna et al. | 378/208 |
| 5,084,908 A | 1/1992 | Alberici et al. | 378/4 |
| 5,591,977 A | 1/1997 | Green et al. | 250/363.03 |
| 6,148,058 A * | 11/2000 | Dobbs | 378/10 |

* cited by examiner

*Primary Examiner*—David P. Porta
(74) *Attorney, Agent, or Firm*—Chien-Wei (Chris) Chou; Oppenheimer Wolff & Donnelly LLP

(57) ABSTRACT

An X-ray computer tomography scanning system for imaging the internal structure of a human being including a source that projects a substantially conically shaped X-ray beam along a path on to a subject such that at least a portion of said beam is transmitted through said subject and a detector array that detects the portion of the beam transmitted through the subject and operative to generate electronic signals in response to the beam transmitted through the subject that projects on to said detector array. The system also including a patient support structure for supporting the subject and rotating said subject about an axis intersecting with and substantially perpendicular to the path of the beam, wherein said subject is constrained such that the subject remains in the path of said beam and an airbag restraining mechanism attached to the support structure for holding the subject in its position. The system includes an imaging mechanism operative to generate an image responsive to the electronic signals generated by the detector.

25 Claims, 8 Drawing Sheets

X-RAY COMPUTER TOMOGRAPHY SCANNING SYSTEM

CROSS-REFERENCE TO RELATED APPLICATIONS

Reference is made and priority claimed from U.S. Provisional Application Ser. No. 60/262,841, filed Jan. 19, 2001, entitled "X-Ray Computer Tomography Scanning System."

BACKGROUND OF INVENTION

1. Field of the Invention

The present invention relates generally to an apparatus and process for medical imaging. More particularly, the present invention relates to medical X-ray imaging systems such as an X-ray computer tomography scanner that includes a subject restraining mechanism and a process for operating thereof.

2. Description of the Prior Art

Computerized tomography is a modern non-invasive technique developed for revealing internal organs and tissues of a human body in cross-section to aid in medical diagnosis, examination, surgery, etc. Essentially an X-ay beam is passed through an imaging subject, e.g. human body, at one location. Part of the X-beam is attenuated by the tissue of the imaging subject, with the remainder of the X-ray beam transmitting through the subject and projecting onto a detector. The detector measures the intensity of the beam transmitting through the imaging subject. The detector then sends electronic signals responsive to the X-ray beam to a computer which calculates and stores the beam intensity for the purpose of reconstructing a graphic image of the subject.

For a measurement at a different location on the subject, the X-ray beam is rotated in one plane to a different angular position and similar measurements are made and recorded. This process is continued for 360 degrees, at which time the computer utilizes the combined measurements recorded to reconstruct a two dimensional image of a cross-sectional slice of the imaging subject. The X-ray beam is then transversely moved by moving the subject and the process repeated to develop another picture of a new cross-sectional slice of the subject. By taking a plurality of such transversely spaced slices and stacking one on top of the other, a three dimensional image of a portion of the subject could be constructed by the computer.

The earliest computerized axial tomography used a pencil beam with a single detector. The beam and the detector were simultaneously rotated and then linearly translated to develop an appropriate scan of the subject. To reduce scanning time a fan-shaped beam replaced the pencil beam and multiple detectors arrayed in an arc were used instead of a single detector. Various detector arrays and detector-beam movements were subsequently developed to increase the speed of the scanning process.

More recent developments in computer tomography employ a source which generates a cone-shaped X-ray beam, instead of the fan-shaped beam, and a two dimensional detector array, instead of a linear array of detectors. This configuration allows the scanning of multiple slices at once. In related industrial applications of computerized tomography disclosed in U.S. Pat. No. 5,023,895, issued to McCroskey, et. al., the use of a cone beam in computer tomography is further improved by rotating a turntable where an object is placed.

None of these systems provide a simple, inexpensive device for scanning the internal organs of a human being. None of these systems provide an acceptable means for restraining a person to prevent movements during the scanning process.

The present invention provides a relatively inexpensive and compact computer tomography system and a process of using the same that rapidly and accurately creates an image of the section of a person under examination.

SUMMARY OF THE INVENTION

One object of the invention is to provide an improved medical computer tomographic system which can rapidly produce accurate images of medical subjects.

Another object of the invention is to provide an improved medical computer tomographic system which can produce accurate images of medical subjects inexpensively.

Another object of the invention is to provide an improved medical computer tomographic system which can produce accurate images of medical subjects without unnecessary discomfort to the subject.

Another object of the invention is to provide an improved medical computer tomographic system which can produce accurate images of medical subjects without performing extensive complex calibration to the x-ray source and detector in the conventional computer tomographic systems.

Yet another object of the invention is to provide an improved medical computer tomographic system which can produce accurate images of medical subjects requiring less complexity of equipment and operation than existing systems.

Briefly, the preferred embodiment includes a source, a detector array, a support structure, a mechanism for rotating the support structure, a restraining mechanism, and an imaging mechanism. The source projects a roughly cone shaped beam of X-ray radiation on to a subject such that a portion of the beam transmits through the subject and projects on to the detector array. The support structure supports the subject and rotates the subject about an axis perpendicular to and intersecting with the X-ray beam such that the X-ray beam continues to project on the subject throughout the support units rotation. The restraining mechanism is attached to the support structure and restrains the subject from unnecessary movement during rotation. The portion of the X-ray beam that transmits through the subject projects on to the detector array. The detector array detects the X-ray beam transmitted through the subject and is operative to generate an electronic signals responsive to the beam transmitted through the subject. The imaging mechanism receives the electronic signals from a detector within the detector array and is operative to generate an image responsive to the electronic signals.

One advantage of the invention is its simple design which requires less equipment than other medical computer tomography scanners and, hence, less maintenance. The system of the present invention does not require the bulky and expensive equipment needed to rotate the detector and X-ray source nor the equipment necessary to feed the subject through the tomography scanner.

Another advantage is that the invention scans the subject in one revolution, whereas prior art systems require multiple rotations due to their use of fan-shaped x-ray beams as opposed to cone-shaped x-ray beams. By using a cone-shaped x-ray beam the present invention eliminates the need to feed the subject through the scanning system.

Yet another advantage of the invention is low cost. The system does not require the expensive mechanism necessary to move the detectors and x-ray source, nor does it require as much calibration as systems that rotate the x-ray source and detector.

Yet another advantage of the invention is the simplified calibration process required to calibrate imaging to compensate for variation produced by the movement of the source and detector. The invention does not require a complex calibration process and is therefore likely to produce sharper images than conventionally calibrated systems. Also the invention will be more reliable because it has fewer components to fail and performs fewer operations reducing the possibility of errors and, hence, requires less maintenance.

The foregoing and other objects, features and advantages of the invention will be apparent from the following detailed description of the preferred embodiments which make reference to the several figures of the drawing.

IN THE DRAWING

FIG. 3b shows the aperture from the view of the plane of line A—A of FIG. 3a;

DETAILED DESCRIPTION OF THE PREFERRED EMBODIMENTS

Figure 1:
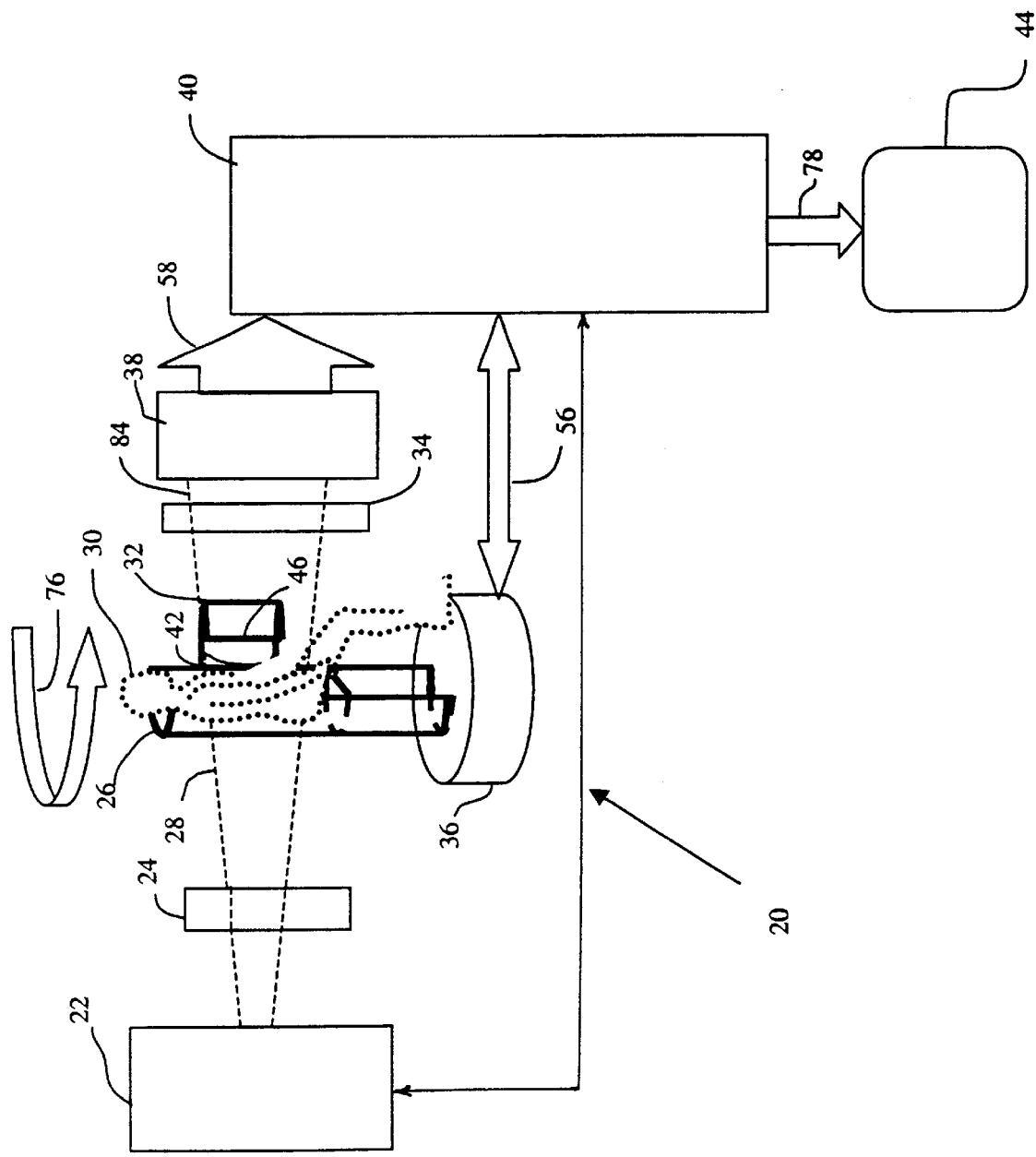
FIG. 1 is a generalized block diagram of a computer tomography system according to an embodiment of the present invention.

The X-ray imaging system of the present invention is an X-ray computer tomography system for imaging the internal organs of a human being or an animal. FIG. 1 is a block diagram illustrating an X-ray computer tomography system 20, according to one embodiment of the present invention for imaging the internal organs of a subject 30. Subject 30 may include the organs of a human being or an animal. The computer tomography system 20 includes a source 22 for projecting a substantially conically shaped X-ray beam 28.

The source 22 is of the type used in medical X-ray imaging as known in the art. The term X-ray may also refer to gamma radiation or other penetrating radiation. The source 22 is positioned such that the beam 28 projected from the source 22, projects along a path onto the subject 30.

In the preferred embodiment, the source 22 is controlled by a computer system 40, such that the source 22 only projects the beam 28 when necessary for imaging. This is done to avoid unnecessary exposure of the subject 30 to harmful radiation.

The path the X-ray beam 28 travels to project onto the subject 30 passes through an aperture 24 which is placed in front of the source 22 between the source 22 and the subject 30. The aperture 24 positions and constricts the X-ray beam 28 by blocking a portion of the beam 28 that is not necessary for imaging the subject 30. The aperture 24 is capable of controlling the size of the beam 28 as well as what part of the subject 30 the beam 28 projects on. By minimizing the beam 28 to a size necessary for imaging the subject 30, the aperture 24 reduces the amount of radiation projects on to the subject 30 and, hence, minimizes the subject 30 exposed under the harmful radiation.

In the preferred embodiment the X-ray beam 28 projects on to the subject 30 after passing through the aperture 24 that constricts the X-ray beam 28. A laser targeting device (not shown) mounted to the source 22 is used to determine the exact path of the X-ray beam 28. The X-ray beam is of sufficient intensity to transmit through the subject 30 and project on to a scintillation screen 34. In the preferred embodiment the computer system 40 controls the intensity of the beam 28 so that it is sufficient to penetrate the subject 30. Alternatively, the beam 28 may be preset to a desired intensity. The intensity used for this type of medical imaging is well known in the art.

The scintillation screen 34 is positioned in front of an array of photodiodes 38 between the array of photodiodes 38 and the subject 30 such that the X-ray beam 28 intersects with the scintillation screen 34. The scintillation screen 34 is positioned such that the path of the X-ray beam 28 is substantially perpendicular to the plane of the scintillation screen 34. The scintillation screen 34 is a rectangularly shaped solid sheet of glass coated with scintillation crystal material. A suitable scintillation crystal would be cesium iodide doped with thalium. The scintillation screen 34 converts X-ray radiation energy into a light energy 84. This technology is well established in the art.

In the preferred embodiment the light energy 84 is transmitted to a photo sensor or a detector (not shown) such as a high-resolution lens system and a charge coupled device (CCD). The light energy 84 is focused by the high-resolution lens system onto the CCD. The CCD, which has a plurality of tiny light-sensitive fields that absorb the light energy 84 after it has passed through the high-resolution lens system, produces electronic signals 58 responsive to the light energy 84 detected by it. An opaque housing covers every surface of the CCD camera 38 except the surface adjacent to the scintillation screen 34 to prevent ambient light from creating false images in the CCD camera 38.

The computer system 40 analyzes the electronic signals 58 to create a shadow image of the subject 30 by analyzing the amount of light energy impinging upon each light sensitive field of the CCD. The more tissue of subject 30 the beam 28 passes through before intersecting with the scintillation screen 34, the less light that is converted by the scintillation screen 34 and the less light that impinges upon a particular light sensitive field of the CCD. The density of the tissue the X-ray beam 28 passes through has a similar affect on the light energy impinging upon a particular light sensitive field of the CCD. The greater the density of tissue the beam 28 passes through, the less light energy that reaches the CCD. The computer stores this shadow image for later manipulation.

A support structure 26 rotates about a vertical axis of the support structure 26 in step increments. This rotation is controlled by the computer system 40 through a control cable 56, such that a shadow image is created by the computer after each increment of rotation. Enough shadow images are created to sufficiently image the subject 30.

The support structure 26 supports the subject 30 during rotation such that the subject 30 remains in the path of the X-ray beam 28.

An airbag restraining mechanism 32 is attached to the support structure 26 with one or more hinges 42 such that the airbag restraining mechanism 32 is capable of rotating about its hinged end to enclose a portion of subject 30 within the support structure 26. The airbag restraining mechanism 32 has a latch 46 on the end opposite its' hinged end, which is secured to the support structure 26 after the subject 30 is enclosed by the restraining mechanism 32. The airbag restraining mechanism 32 serves to restrain the subject 30 from unnecessary movement during the rotation 76 of the support structure 26. Movement of the subject 30 during scanning can reduce image quality by altering subject geometry from one position or angle to another. The computer system 40 creates a tomographic image by compiling data from the shadow images created for each angular increment of rotation. If the geometry of the subject 30 varies significantly between shadow images the computer system 40 will be unable to create an accurate tomographic image. By restraining the subject 30 during the scanning process, the airbag restraining mechanisms 32 improves image accuracy. In alternative embodiment, other restraining mechanism such as a belt may be substituted for the airbag.

A rate table 36 contains an electric motor which rotates the support structure 26 about the vertical axis. This motor is controlled by the computer system 40 through the control cable 56. After each shadow image is captured the computer system 40 sends a signal through control cable 56 to the rate table 36 to advance the motor to rotate the rate table 36 and the patient support structure 26 by another increment. This process continues until completing the entire image capturing process.

The computer system 40 controls the timing of projecting X-ray beam 28 generated by the source 22. In an alternative embodiment, the aperture 24 may be manually adjusted. The computer system 40 uses the electronic signals 58 from the array of photodiodes 38 to generate an image. The computer system 40 subsequently stores the image in a data storage device (not shown), such as a magnetic hard disk drive or a semiconductor memory, in the computer system 40. The computer system 40 then rotates the subject 30 by sending electrical pulses to the motor in the rate table 36, projects another X-ray beam 28 and creates another image. The computer system 40 continues this process until enough shadow images have been stored to create a complete tomographic image through a method of back projection.

The computer system 40 uses all of the images stored to create a tomographic image by a process of back projection image reconstruction. The process of back plane image reconstruction is well known in the art. The difference between the present invention and the prior art for the medical use of X-ray tomographic back plane projection imaging is that the present invention effectively scans multiple slices at once compared to the prior art. Prior art medical devices used a fan shaped X-ray beam with a linear detector array while the present invention uses a conical shaped beam 28 with a two dimensional detector array 38. Each row 93 (See FIG. 4) scanned by the present invention is the equivalent of a slice taken in the conventional process. This arrangement in the present invention allows it to scan a subject 30 in one rotation instead of multiple rotations combined with the feeding of the patient through the scanning device as required by the prior art technologies. The present invention uses a method of back projection similar to the one described in U.S. Pat. No. 5,023,895, which is incorporated by reference herein.

The computer system 40 performs calibration for the scanning system by storing an image with a calibration unit in place of the subject 30 without the rotation of the subject. The computer system 40 then corrects each image of the calibration unit taken at each increment of rotation using the stored image. This correction consists of subtracting anomalous images contained in the image taken at each increment of rotation without the subject 30 from each image taken at each rotation with the subject 30.

The computer system 40 transmits the tomographic image to a display 44 in the form of an electronic data signal 78. The display 44 is a computer monitor and/or printer. Display output may be further processed in the form of two dimensional slice images or three dimensional images.

Figure 2:
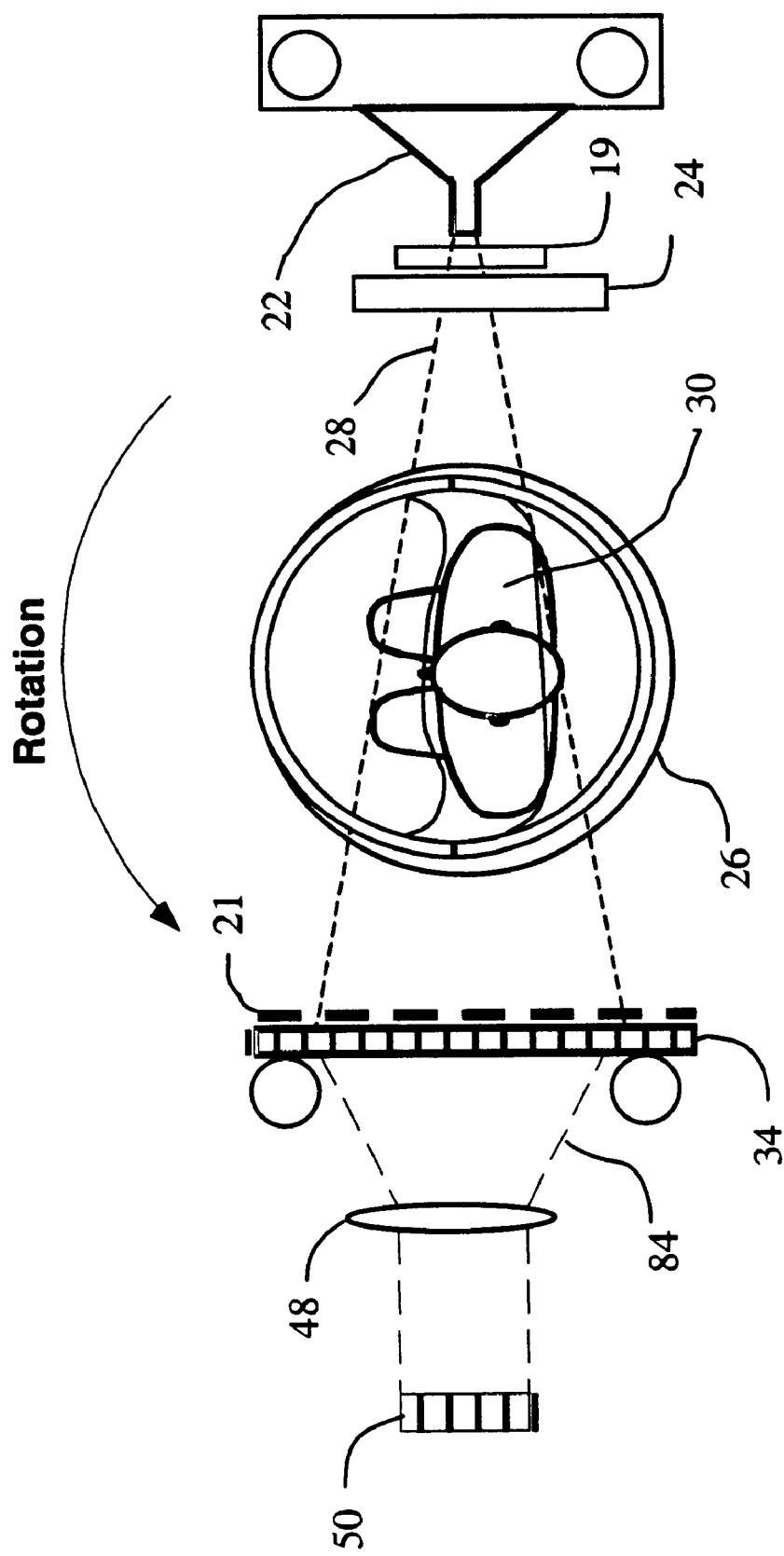
FIG. 2 is a generalized diagram of the scanning system depicting the rotating subject relative to the X-ray beam and the detector from a top view according to one embodiment of the present invention.

FIG. 2 illustrates an alternative embodiment of the present invention, in which an optical system is used to scan the subject 30. In the alternative embodiment the source 22 projects an X-ray beam 28 through a first filter plate 19 positioned between the source 22 and an aperture 24. A first filter in the first filter plate reduces the X-ray energy level by absorbing low energy portions of the X-ray beam. The first filter plate 19 further serves to normalize the X-ray beam energy distribution with a varying thickness corresponding to the predetermined energy distribution of the X-ray beam 28. Areas of the first filter plate 19 intercepting higher energy parts of the X-ray beam 28 are of greater thickness to absorb more energy so that the X-ray beam 28 transmitting through first filter plate 19 is of a more even energy distribution across its projected area. The first filter plate 19 could also be positioned between the aperture 24 and the subject 30. After passing through the first filter plate 19, the X-ray beam 28 is focused by the aperture 24 on to the subject 30. The X-ray beam 28 is projected such that a portion of the beam 28 is absorbed by the tissue of the subject 30 and a portion of the beam 28 transmits through the subject 30 and impinges upon a second filter plate 21 which serves to reduce the affects of scatter radiation by absorbing low energy portions of the X-ray beam. The second filter plate 21 is mounted in front of the scintillation screen 34 between the scintillation screen 34 and the subject 30 and is perpendicular to the path of the X-ray beam 28.

After passing through the second filter plate 21 the X-ray beam 28 impinges upon the scintillation screen 34. The scintillation screen 34 converts the X-ray beam 28 to a visible light beam 84, and projects the visible light beam 84 through a lens 48 and onto a photo sensing array 50 such as a CCD in a digital camera described above. The images recorded by the digital camera are then processed by the computer system 40 as if they were the electronic signals 58 of the preferred embodiment as shown in FIG. 1. Optical systems are made-up of three basic components, which may vary greatly from system to system: the scintillation screen 34, which converts x-rays to a visible image; an optical transfer mechanism (usually a lens and mirror, or a fiber optic coupler) 48, which transfers the image to a recording device, with as little loss of information as possible; and a photo sensing array 50 (usually a CCD in a digital camera).

Figure 3A:
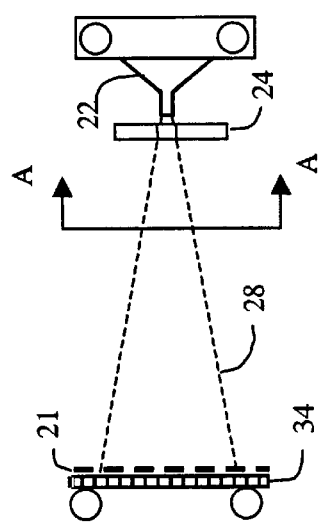
FIG. 3a shows an exemplary embodiment of the aperture of the preferred embodiment of the present invention.

FIG. 3*a* shows an exemplary embodiment of the aperture 24 of the preferred embodiment of the present invention. The source 22 projects an X-ray beam 28 through an aperture 24.

Figure 3B:
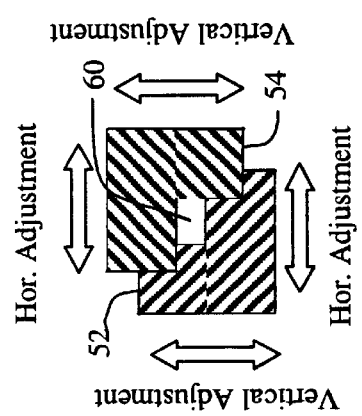

FIG. 3b shows the aperture 24 from the view of the plane of line A—A of FIG. 3. The aperture 24 comprises a first plate 52 and a second plate 54, which are opaque to radiation. Such plates would typically be made of lead or other dense material. First plate 52 and second plate 54 intersect such that they form an opening 60 through which the X-ray beam 28 passes before impinging upon the subject 30. The shape of the X-ray beam 28 is thus defined by the shape of the intersection of the first plate 52 and second plate 54. To facilitate changes in the size and focus of the X-ray beam, a positioning mechanism is attached to first plate 52 and second plate 54. Either first plate 52 or second plate 54 can be adjusted horizontally or vertically to define the size and position of the opening 60.

Figure 4:
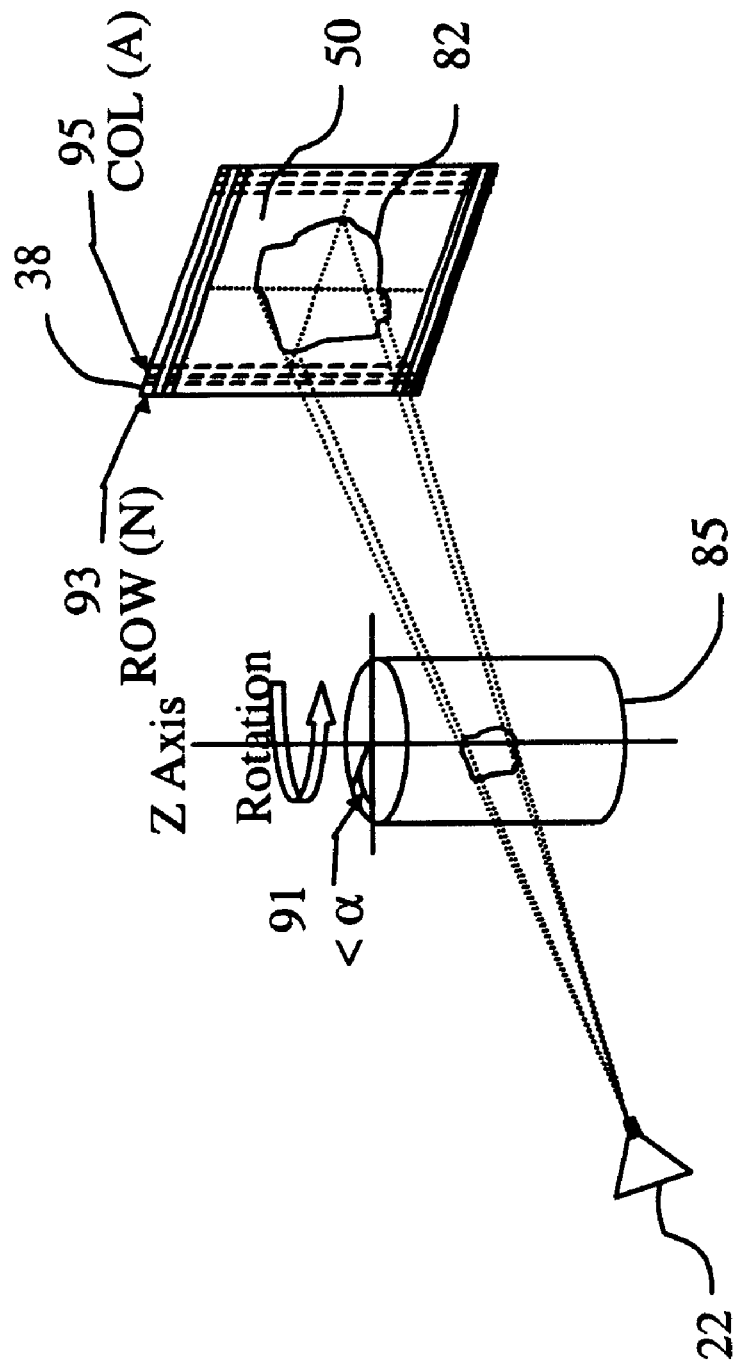
FIG. 4 is a diagram illustrating the projection of the x-ray beam through a scanning subject and onto the detector array according to one embodiment of the present invention.

FIG. 4 illustrates the projection of the x-ray beam 28 (FIGS. 1 and 2) through a scanning subject 30 (FIGS. 1 and 2) and onto the photo sensing array 50 according to one exemplary embodiment of the present invention. The area occupied by the subject 30 throughout rotation is shown as a solid object 85. The X-ray beam 28 has a peripheral configuration 82 which is simply the border of the projected area of the X-ray beam 28. The peripheral configuration 82 of the X-ray beam 28 is shown as it projects through the volume 85 occupied by the subject 30 and impinges upon the photo sensing array 50. The peripheral configuration 82 of the X-ray beam 28 strikes a plurality of rows 93 and columns 95 in the photo sensing array 50 effectively scanning a plurality of rows (slices) 93 simultaneously.

Figure 5:
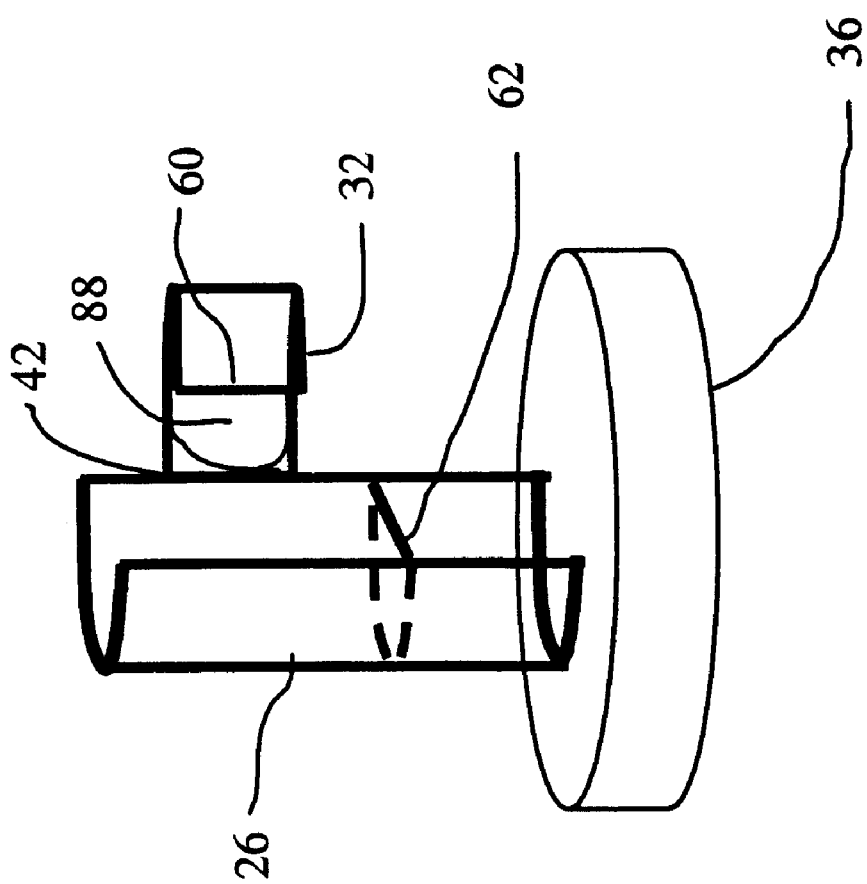
FIG. 5 depicts one configuration of the support structure and airbag restraining mechanism as claimed in the present invention.

FIG. 5 shows the patient support structure 26 of the preferred embodiment of the present invention. The patient support structure 26 is constructed of material substantially transparent to X-ray radiation. Such materials include low density plastic structures or other low density materials. The patient support structure 26 is of a semi-cylindrical shape approximately five feet in height.

The inside surface of the patient support structure 26 which the back of the subject 30 rests against is shaped to conform to the shape of the back of the subject 30, such that pressing the subject 30 against the back of the patient support structure 26 restrains the subject from unnecessary movement during rotation.

The inside surface of the patient support structure 26 is padded with material substantially transparent to X-ray radiation such that a subject 30 is comfortably supported during the scanning process. Such materials include low density foam polymer such as neoprene or foam rubber.

A removable adjustable seat 62 is attached to the patient support structure 26 by being inserted into slots in the patient support structure 26. The patient support structure 26 contains several slots at various heights to accommodate imaging at different heights. The slots are semi-circular and horizontal occupying the inner surface of the patient support structure 26. The slots are slightly thicker than the edge of the seat 62 such that the seat 62 can be inserted without excessive force and remain in place when occupied by a subject 30. The seat 62 is padded for comfort.

The airbag restraint mechanism 32 is made up of an outer cup 60 and an inner airbag 88. The cup 60 is composed of a material substantially transparent to X-ray radiation. The cup 60 is semi-cylindrical in shape and hinged through a plurality of hinges 42 to the patient support structure 26 on one edge of the cup 60. The hinges 42 allow the cup 60 to rotate about the hinges 42 such that the edge of the cup 60 opposite the hinged edge of the cup 60 contacts the patient support structure 26 and the two form a closed circle. The edge of the cup 60 opposite the hinges 42 can be secured to the patient support structure 26 with a latch 46. Both the hinges 42 and the latch 46 can be attached at different heights on the patient support structure 26 thereby allowing for restraint at different vertical positions.

The airbag 88 is attached to the inner surface of the cup 60 such that when the cup 60 encloses the subject 30, the airbag 88 is located between the subject 30 and the cup 60. The airbag 88 is constructed of a material substantially transparent to X-ray radiation such as a low density plastic such as polyurethane or nylon. Other low density materials such as latex or neoprene would also be suitable.

When imaging is about to commence the airbag 88 is inflated to a pressure sufficient to restrain the subject 30 from unnecessary movement during rotation. Any substance behaving substantially as a fluid is suitable to inflate the airbag 88, air being the safest and most cost effective.

In an alternative embodiment, the airbag 88 may be replaced with other restraining mechanism means, such as a belt, a strap or a fastener.

The support structure 26 is mounted on a rate table 36 which can be constructed of any rigid material. The rate table 36 contains an electric motor (stepper, servo or DC motor) for rotating the patient support structure 26 about the center of the rate table 36 to precisely preset positions. The electric motor is controlled by the computer system 40 through control cable 56 (FIG. 1). The patient support structure 26 is attached to the rate table 36 such that the two form a single unit.

Figure 6:
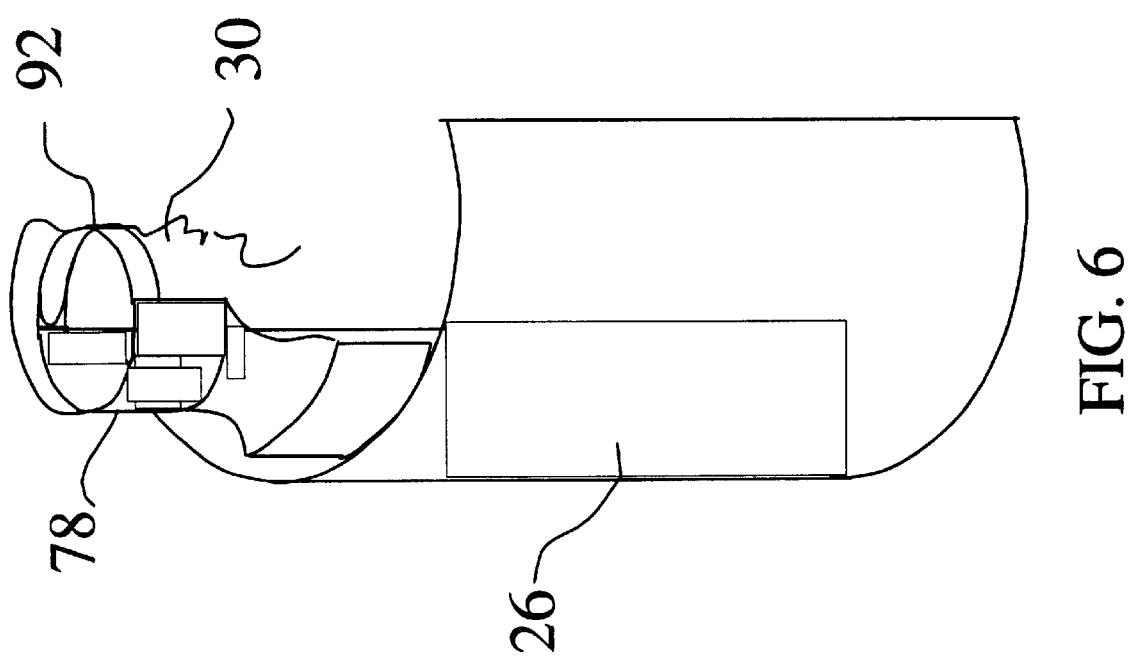
FIG. 6 depicts one configuration of the head restraint relative to the support structure as claimed in an embodiment of the present invention.

FIG. 6 shows a head restraint included in one embodiment of the present invention comprising a head support structure 78 which is attached to the support structure 26 with fasteners such that it can be easily removed. The head support structure 78 is constructed of a material substantially transparent to radiation such as a low density plastic or cloth. The head support structure 78 extends above the patient support structure 26 as shown in FIG. 6.

The top portion of the head support structure 78 forms a semi-cylindrical shell with similar function to the patient support structure 26. The top portion of the head support structure 78 is padded similarly to patient support structure 26 such that the head of the subject is restrained from unnecessary motion when pressed against the head support structure 78.

A strap 92 is used to secure the forehead of the subject 30 against the head support structure 78 such that the subject's head is restrained from unnecessary movement during rotation and scanning processes.

Alternatively a device similar in operation to the airbag restraining mechanism 32 could be employed to secure the head of the subject 30 to the head support structure 78. Such a device would have to constructed such that the airbag contained therein did not overly pressure the soft tissue of the face.

Figure 7:
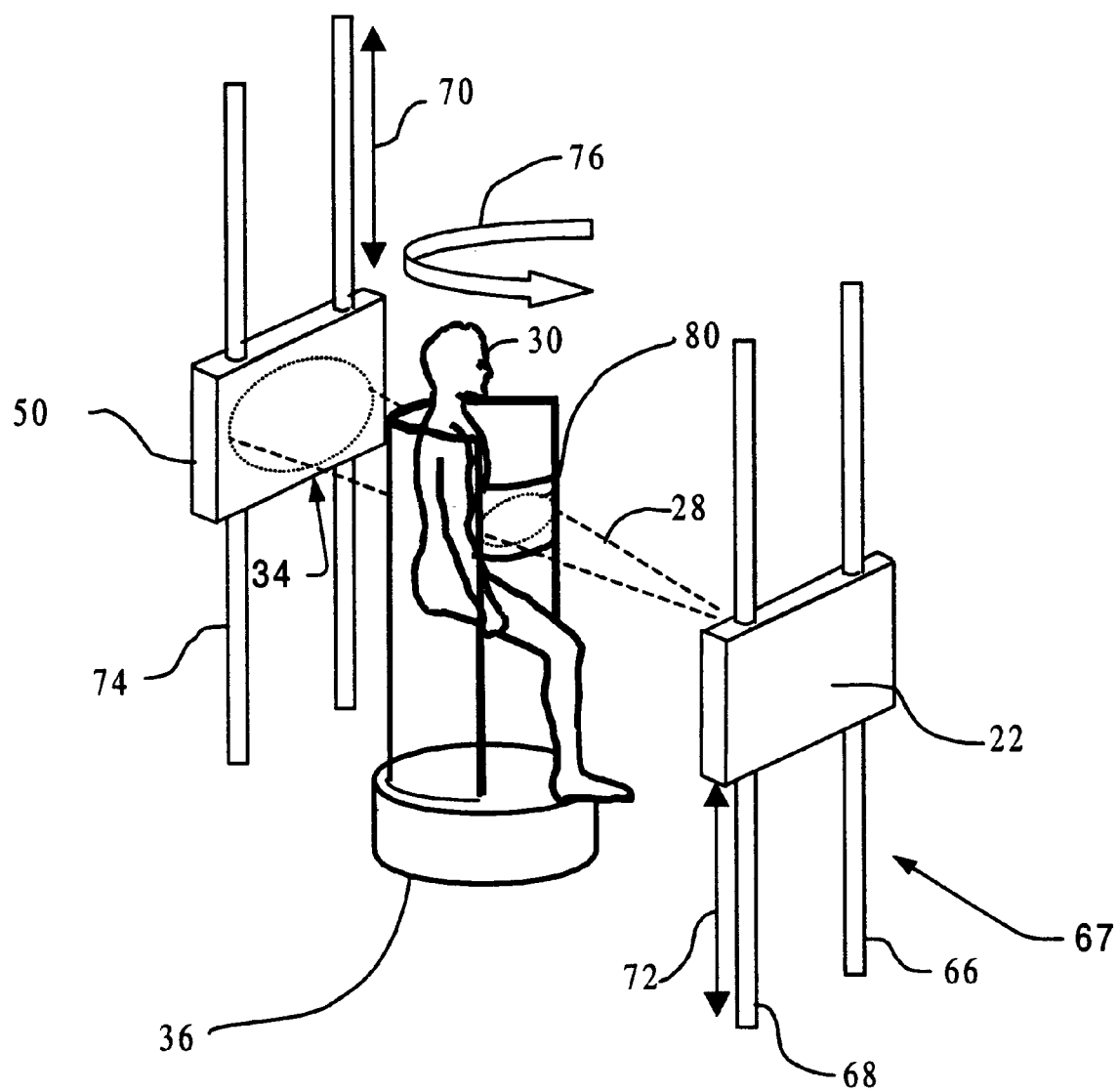
FIG. 7 illustrates one configuration for the source support mechanism and detector support mechanism relative to the support structure as claimed in one embodiment of the present invention.

FIG. 7 shows an exemplary embodiment of the present invention utilizing height adjustment for scanning at different height positions. The source 22 is mounted on a source support mechanism 67. The source support mechanism 67 comprises two cylindrical rails 66, 68 on which the source 22 can move vertically 72.

A manual or automated device is operative to elevate and lower the source 22 and a second such device is operative to elevate and lower the detector array 50. Such elevator devices are commercially available through many sources. The source support mechanism 67 uses a mechanism to hold the x-ray source in position on the rails at the appropriate height for scanning.

The detector array 50 is mounted to a detector support mechanism 74. The detector support mechanism 74 functions similarly to the source support mechanism 67, except that the detector array 50 is locked into positions instead of the source 22. An elevator device is also used to move the scintillation screen 34 vertically 70. The height positions of the detector support mechanism 74 correspond precisely to the height positions of the source support mechanism 67, such that the source 22 remains stationary relative to the detector array 50. This structure reduces the amount of calibration that is unnecessary artifacts normally introduced in a conventional computer tomography system to reposition the source 22.

Auto-calibration is preformed by fixing the relationship between the X-ray source 22 and detector array 50 constant. A laser targeting device(not shown) mounted to the source 22 is used to align the detector array 50. The distribution of X-ray energy is predetermined and normalized between the different detectors within the array 50. In addition, the detector sensitivity among the detectors within the array 50 can also be predetermined and normalized. Each shadow image created is corrected with the predetermined image corrections to account for anomalies due to the relative position of the source 22 and photo sensing array 50.

Figure 8:
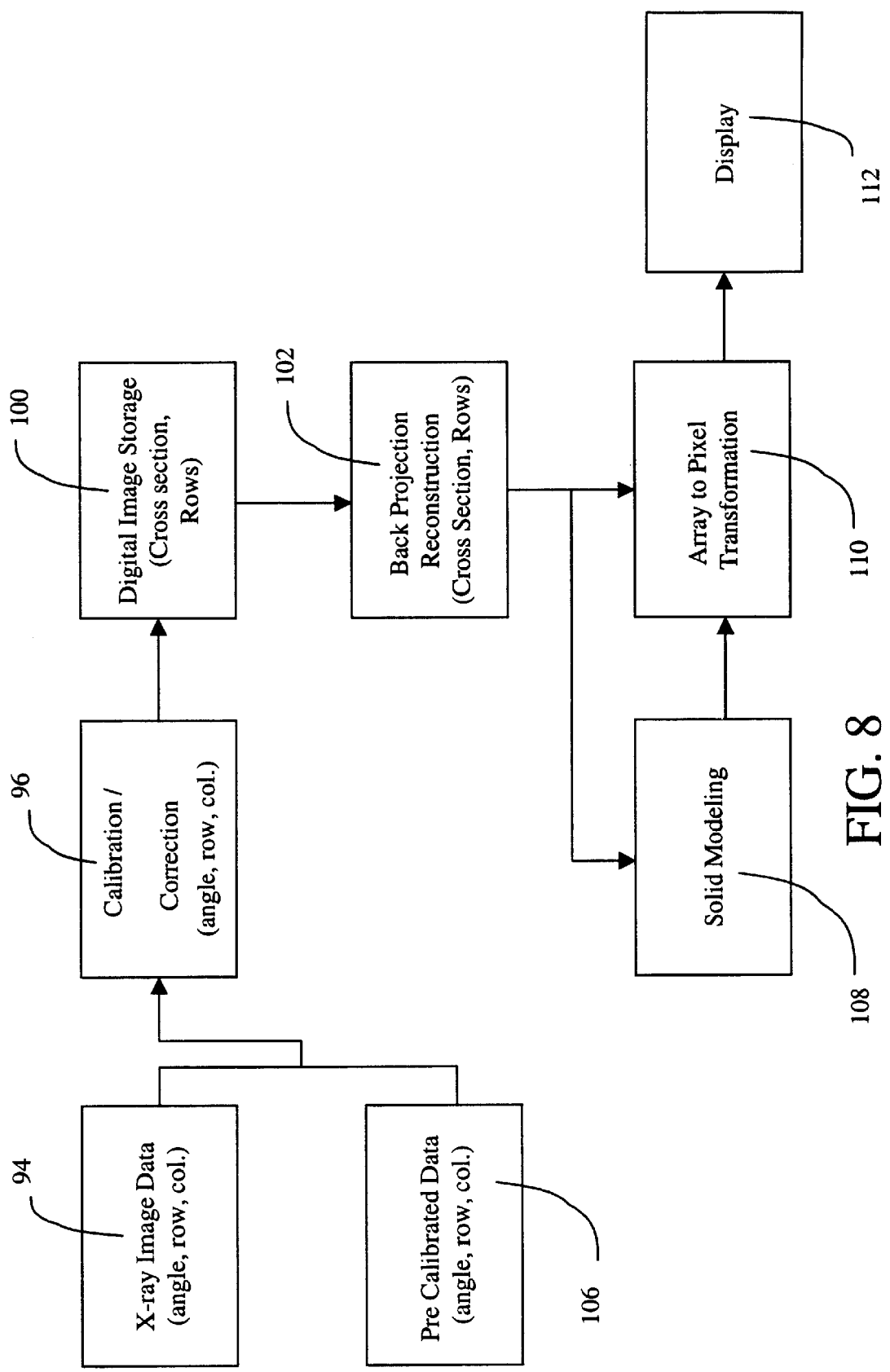
FIG. 8 is a block diagram illustrating a process flow for generating images in one embodiment of the present invention.

FIG. 8 is a block diagram illustrating a process flow for generating images in one embodiment of the present invention. Electronic signals 58 are read by the computer system 40 as image data 94 representing X-ray beam 28 intensity at each row 93 and column 95 and angular increment of rotation 91 (see FIG. 4). The image data 94 undergoes calibration 96 by correcting the image data 94 to compensate for aberrant measurements by comparing it to pre-calibrated data 106. Pre-calibrated data 106 are intensity measurements taken before a subject 30 is introduced. This data 106 is compared to the image data 94 to compensate for uneven energy distribution in the X-ray beam 28. The corrected image data 94 is then stored electronically.

After all necessary corrected image data 94 has been stored, the compiled data 94 is combined and subjected to back projection 102 to create a tomographic image. Back projection 102 is an established method of constructing tomographic images. The tomographic image then undergoes array to pixel transformation 110 and is converted to a pixel image which can portray the tomographic image as either a two dimensional cross section or a three dimensional object. The pixel image is then displayed on a display 112 such as a color computer monitor or cathode ray tube.

Although the present invention has been described in terms of specific embodiments, it is anticipated that alterations and modifications thereof will no doubt become apparent to those skilled in the art. It is therefore intended that the following claims be interpreted as covering all such alterations and modification as fall within the true spirit and scope of the invention.

What is claimed is:

1. A computer tomography scanning system comprising:
   a source that projects a substantially conically shaped X-ray beam along a path on to a subject such that at least a portion of said beam is transmitted through said subject;
   a detector array that detects the portion of the beam transmitted through the subject and operative to generate electronic signals in response to the beam transmitted through the subject that projects on to said detector array;
   a patient support structure for supporting the subject and rotating said subject about an axis intersecting with and substantially perpendicular to the path of the beam, wherein said subject is constrained such that the subject remains in the path of said beam;
   an airbag restraining mechanism attached to the support structure for holding the subject in its position; and
   an imaging mechanism operative to generate an image responsive to the electronic signals generated by the detector.

2. The computer tomography scanning system as recited in claim 1, further comprising:
   an aperture that limits the amount of unnecessary radiation projected on the subject by controlling the peripheral configuration of the beam, said aperture being located in the path of the beam between the source and the subject, thereby allowing the beam to irradiate only the portion of the subject to be imaged.

3. The computer tomography scanning system as recited in claim 1, further comprising:
   an energy filter for reducing low energy radiation and second order effects of the X-ray beam, said energy filter being located in the path of the X-ray beam, between the source and the detector.

4. The computer tomography scanning system as recited in claim 3, wherein the energy filter further comprises:
   a filter plate for normalizing the X-ray beam intensity, said filter plate having a varied thickness corresponding to the intensity of the X-ray beam intersecting each portion of said filter plate, thereby causing the X-ray beam intensity to be nearly uniform across its projecting area.

5. The computer tomography scanning system as recited in claim 2, wherein the aperture further comprises:
   a plurality of plates, each being substantially opaque to radiation; and
   a positioning mechanism for controlling the peripheral configuration of the beam by positioning the plates so as to constrain the periphery of the beam, said plates intersecting in such a way as to form an opening through which the constrained beam projects.

6. The computer tomography scanning system as recited in claim 1, wherein the airbag restraining mechanism further comprises:
   a securing mechanism for securing the airbag restraining mechanism about the subject such that the subject is secured to the support structure during rotation.

7. The computer tomography scanning system as recited in claim 6, wherein the airbag restraining mechanism further comprises:
   an inflation mechanism capable of inflating the airbag to a sufficient pressure to hold the subject against the support structure during rotation.

8. The computer tomography scanning system as recited in claim 1, wherein the subject includes a head and wherein the airbag restraining mechanism further comprises:
   a head restraint for restraining the head of the imaging subject during rotation.

9. The computer tomography scanning system as recited in claim 8, wherein the head restraint further comprises:
   a head support attached to the support structure for supporting the head of the imaging subject; and
   an airbag attached to said head support for holding the head of the subject against the head support during rotation, said airbag enveloping at least a portion of the head, thereby gently holding the head of the subject against the head support during rotation.

10. The computer tomography scanning system as recited in claim 9, wherein the head restraint further comprises:
an inflation mechanism for inflating the airbag to a sufficient pressure to restrain the head of the subject against the head support during rotation, thereby gently restraining the head of the imaging subject during rotation.

11. The computer tomography scanning system as recited in claim 1, wherein the support structure further comprises:
a seat for the subject to sit on during rotation, the seat being removable to allow the imaging subject to stand during rotation.

12. The computer tomography scanning system as recited in claim 1, wherein the detector further comprises:
a two dimensional scintillation screen operative to generate a light beam responsive to the portion of the X-ray beam transmitted through the subject that projects on said scintillation screen; and
a two dimensional array of photosensitive devices operative to generate electronic signals responsive to said light beam, said array being positioned so as to intercept the light beam generated by the scintillation screen.

13. The computer tomography scanning system as recited in claim 12, wherein the detector further comprises:
an optical mechanism for focusing the light beam generated by the scintillation screen upon the array of photosensitive devices, said optical mechanism being positioned so as to intersect the light beam generated by the scintillation screen and focus the light beam upon the array of photosensitive devices.

14. The computer tomography scanning system as recited in claim 1, wherein the detector further comprises:
a two dimensional array of X-ray detectors operative to generate electronic signals responsive to the portion of the X-ray beam transmitted through the subject that projects on said array of X-ray detectors.

15. The computer tomography scanning as recited in claim 1, further comprising:
a source support mechanism for supporting the source at one of several height positions, said source support mechanism holding said source rigidly at any one of said height positions; and
a detector support mechanism for supporting the detector at one of several height positions corresponding to the height positions of the source support mechanism, said detector support mechanism holding the detector rigidly at any one of said height positions, thereby allowing for imaging at different heights with the source and detector remaining stationary relative to each other.

16. The computer tomography scanning system as recited in claim 1, wherein the medical imaging system further comprises:
an auto-calibration mechanism for normalizing X-ray beam energy distribution by fixing the position of the source relative to the detector and adjusting the image generated by the imaging mechanism to compensate for variations in X-ray beam intensity and detector sensitivity.

17. The computer tomography scanning system as recited in claim 1, wherein the imaging mechanism further comprises a 3D imaging device operative to generate three dimensional images responsive to the electronic signals generated by the detector.

18. A method of generating an image, comprising:
restraining a subject from unnecessary movement relative to a support structure using an airbag restraining mechanism;
rotating the support structure; and
projecting a substantially conically shaped X-ray beam along a path intersecting with and substantially perpendicular to the axis of rotation of said support structure, on to said subject such that a portion of the X-ray beam transmits through the subject and projects on to a detector;
measuring the portion of the X-ray beam that projects on to said detector;
generating an image responsive to the measurements of the X-ray beam transmitted through the subject that projects on to the detector.

19. The method of claim 18, further comprising:
reducing the imaging subjects exposure to unnecessary radiation by controlling the peripheral configuration of the X-ray beam projected on to said subject.

20. The method of claim 19, wherein controlling the peripheral configuration of the X-ray beam further comprises:
providing a plurality of plates, which are substantially opaque to radiation; and
positioning said plates directly between the source and the subject in such a way as to form an opening through which only a portion of the X-ray beam may pass to irradiate the subject.

21. The method of claim 20, wherein restraining the subject further comprises:
inflating the airbag restraining mechanism such that the subject is held against the support structure to preventing unnecessary movement of the subject as the support structure rotates, thereby gently restraining the subject during rotation.

22. The method of claim 18, wherein the imaging subject includes a head and wherein restraining the imaging subject further comprises:
restraining the head of the imaging subject.

23. The method of claim 22, wherein restraining the head of the imaging subject further comprises:
providing a head support attached to the support structure for supporting the head of the subject during rotation;
placing the head of the imaging subject against the support structure;
securing an airbag to the head support such that the airbag encloses at least a portion of the head against the head support; and
inflating the airbag such that the head of the subject is restrained from unnecessary movement as the subject is rotated, thereby gently restraining the head of the subject during rotation.

24. The method of claim 18, wherein scanning an imaging subject includes auto-calibration comprising:
providing a source for a three dimensional X-ray beam;
providing a detector array for detecting a three dimensional X-ray beam;
fixing the position of the source;
fixing the position of the detector array;
projecting a three dimensional X-ray beam on the detector array from the source;
measuring the X-ray beam with the detector array;
calculating the variations in measurements across the detector array; and
normalizing the sensitivity of the detector array to compensate for the variations in the measurements across the detector array, thereby minimizing the effects of beam intensity variation and detector sensitivity variation on imaging as well as reducing interference from a restraining mechanism on imaging.

25. The method of claim 18, wherein generating an image further comprises:

generating a three dimensional image responsive to the measurements of the X-ray beam transmitted through the subject that project on to the detector.

* * * * *